United States Patent [19]
Darby

[11] Patent Number: 5,491,909
[45] Date of Patent: Feb. 20, 1996

[54] SHOCK ABSORBING MEDICAL SHOE

[75] Inventor: H. Darrel Darby, Huntington, W. Va.

[73] Assignee: Darco, Huntington, W. Va.

[21] Appl. No.: 107,577

[22] Filed: Aug. 18, 1993

[51] Int. Cl.⁶ .................................................. A43B 13/18
[52] U.S. Cl. .................................. 36/28; 36/110; 36/76 R
[58] Field of Search .................................. 36/73, 88, 89, 36/92, 106–108, 110, 11.5, 25 R, 28, 30 R, 7.5, 68, 69, 76 R, 76 C, 140, 174–177, 180, 182, 96, 108; 602/10, 3, 23, 27

[56] References Cited

U.S. PATENT DOCUMENTS

| | | | |
|---|---|---|---|
| 872,615 | 12/1907 | Eastman | 36/107 |
| 1,402,834 | 1/1922 | Bunch | 36/177 |
| 3,237,319 | 3/1966 | Hanson | 36/89 |
| 4,385,456 | 5/1983 | Livernois et al. | 36/89 |
| 4,414,759 | 11/1983 | Morgan et al. | 36/110 |
| 4,638,576 | 1/1987 | Parracho et al. | 36/68 |
| 4,677,767 | 7/1987 | Darby | 36/110 |
| 4,794,707 | 1/1989 | Franklin et al. | 36/107 |
| 5,052,128 | 10/1991 | Lonardo | 36/110 |
| 5,088,481 | 2/1992 | Darby | 36/11.5 |

Primary Examiner—Thomas P. Hilliard
Attorney, Agent, or Firm—Sughrue, Mion, Zinn, Macpeak & Seas

[57] ABSTRACT

A shoe for use on a post-operative, traumatized, diabetic or insensitive foot includes a shock absorbing sole material, with an insole of shock absorbing foam that contours to and supports the sole of the foot, and being regulated in flexibility by a metatarsal shank that limits the amount of flexibility under the metatarsophalangeal joint to provide controlled support to that area. This sole is of a special rocker design that allows the wearer to roll through the gait cycle without placing undue pressure on the heel and forefoot. The upper material consists of an outer wall of breathable, nylon mesh material lined with a soft, conforming material, reinforced at the heel by a heel cup that provides lateral stability. The heel cup is lined from the top by a full-length heel collar that conforms to the Achilles Triangle of the user, providing padding to the achilles tendon and under the malleoli, while at the same time making it impossible for the heel to slip out of the shoe during ambulation. The forward position of the upper is designed with two flaps that extend up either side of the front of the foot and fasten onto each other by means of hook and loop fastening material strips, eliminating the need for exterior straps, rings and buckles, which can cause pressure sores on the dorsum of the foot in many cases. The flaps provide a complete cover for the dorsal aspect of the foot.

2 Claims, 3 Drawing Sheets

5,491,909

SHOCK ABSORBING MEDICAL SHOE

FIELD OF THE INVENTION

The present invention pertains to post-operative surgical shoes and other shoes that are designed to accommodate forefoot deformities and bulky dressings, and more particularly to such shoes which are capable of being adjustably contoured for cradling the bone structure of the foot during healing.

BACKGROUND OF THE INVENTION

Following surgery or other injury to the foot, when ulcerations or other skin lesions are present, or when forefoot deformities do not allow standard footwear to be worn, accommodative footwear is needed to provide adequate protection and support. There are many problems with existing products, including heel slippage due to an overly rigid sole, a flat sole or inadequate heel cushioning, inadequate protection for the metatarsal due to excessive flexibility in the front portion of the sole, and, in the case of flat-soled shoes, a tendency for older patients who shuffle when they walk to fall when the toe catches on deep carpeting. In addition, many shoes on the market are made with complicated closures that make it difficult for older patients or arthritic patients to open and close the shoe and do not allow the doctor to have easy and immediate access to the forefoot for examination after surgery or trauma.

It is therefore a primary objective of the present invention to eliminate the above-mentioned problems and provide a more stable and protective shoe that supports the traumatized foot and accommodates the foot when standard footwear cannot be worn due to dressing size, swelling, forefoot deformities, or the use of bulky forefoot splints or insoles.

SUMMARY OF THE INVENTION

The above and other objects of the invention, which will become apparent hereinafter, are achieved by the provision of a surgical shoe having a molded outer sole similar to those of conventional running shoes with a rounded heel and toe to reduce the shock incurred in heel strike and weight bearing pressures of toe-off; a metatarsal shank located between the inner and outer soles that supports the metatarsophalangeal joints after trauma or surgery and helps reduce pressure to the plantar aspect of the foot to speed healing of ulcerations and other lesions; an inner sole of a shock absorbing foam material that conforms to the plantar aspect of the foot; an upper of breathable mesh material lined with a foam that conforms to and cushions the foot with forward flaps that fold over the forefoot and attach to each other without straps; and a heal cup that provides stability and reduces pronation and which is lined with a full heel collar that conforms to the Achilles Triangle to eliminate heel slippage and reduce friction against the achilles tendon and under the malleoli.

For a more complete understanding of the invention and the objects and advantages thereof, reference should be made to the following detailed description and the accompanying drawings wherein a preferred embodiment of the invention is described and illustrated.

DESCRIPTION OF THE PREFERRED EMBODIMENT

Figure 1:
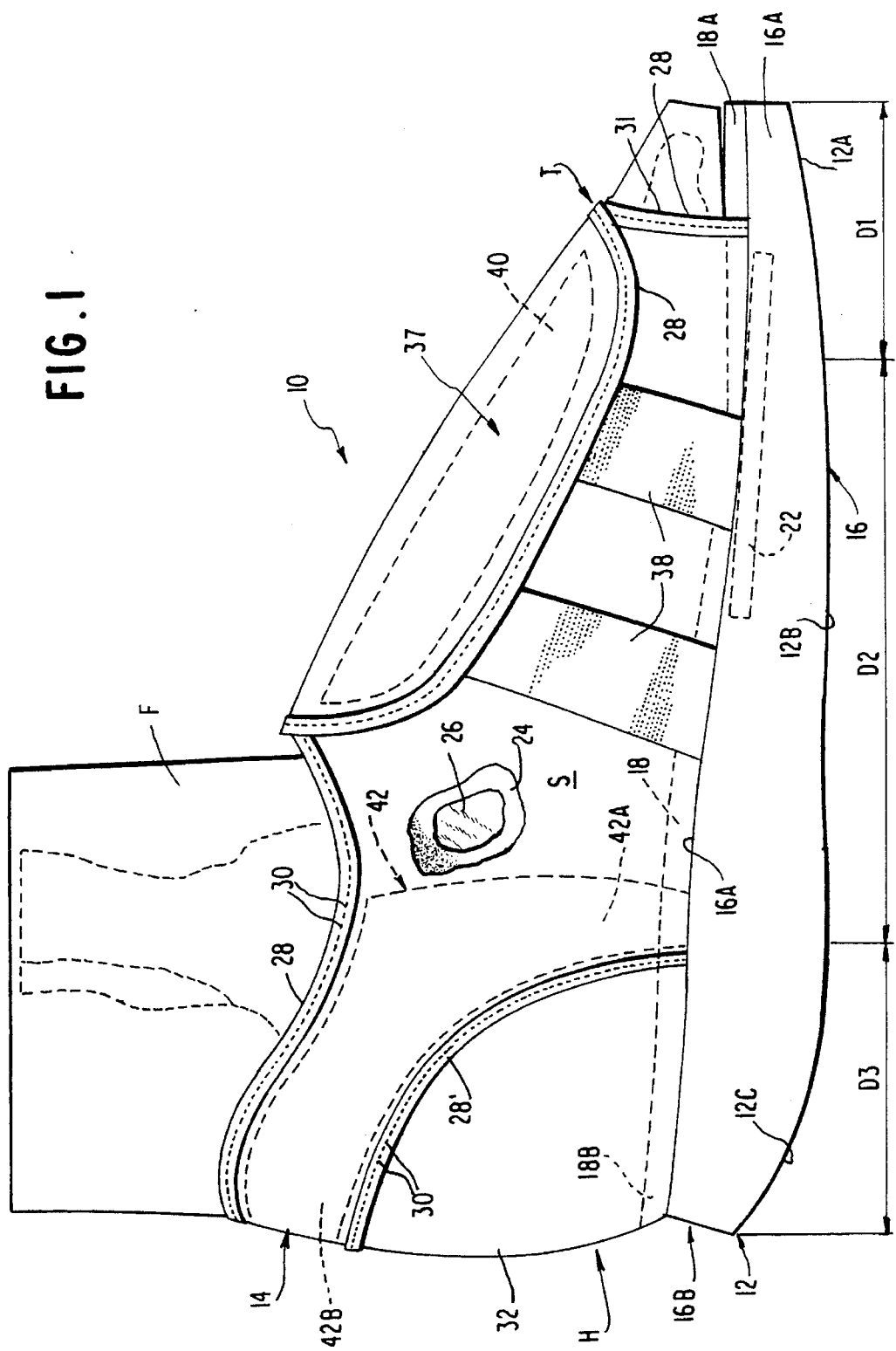
FIG. 1 is a side elevational view of a post-operative medical shoe forming a preferred embodiment of the present invention.
Figure 2:
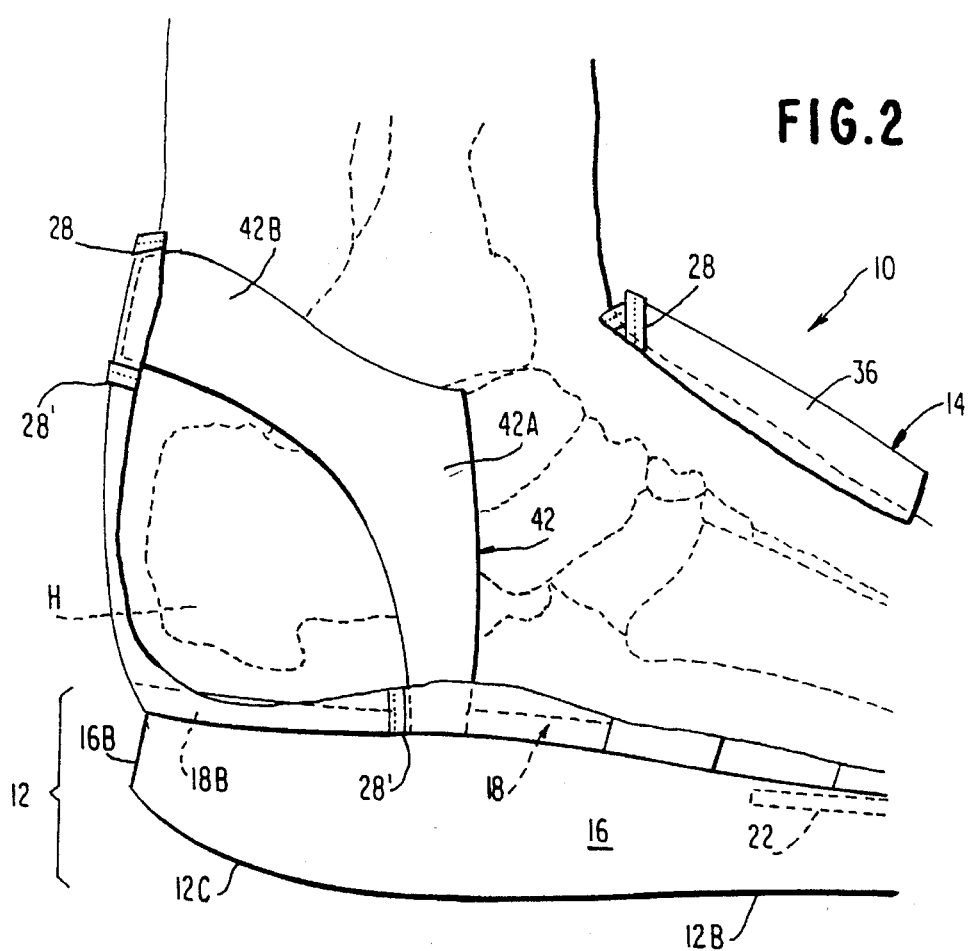
FIG. 2 is a cut-away view of the heel area of the post-operative medical shoe showing placement of the heel collar and demonstrating how the heel collar conforms to the Achilles Triangle.
Figure 3:
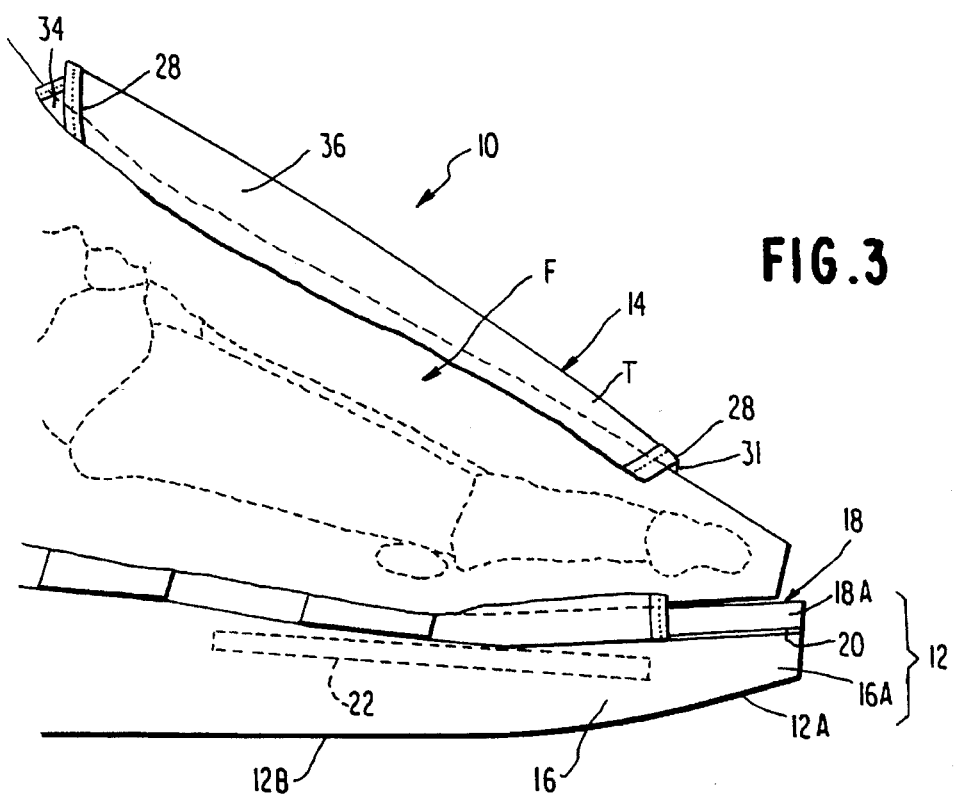
FIG. 3 is a cut-away view of the forefoot of the post-operative medical shoe showing the placement of the metatarsal shank.

The shock absorbing medical shoe of this invention is an outgrowth of post-operative medical shoes exemplified by U.S. Pat. No. 4,677,767, issued Jul. 7, 1987 to H. Darrel Darby and entitled "SHOCK ABSORBING SURGICAL SHOE" and U.S. Pat. No. 5,138,777, issued Aug. 18, 1992 to H. Darrell Darby and entitled "POST-OPERATIVE SHOES FOR USE AFTER FOREFOOT SURGERY". Referring to the drawings, FIGS. 1–5, the shock absorbing medical shoe, indicated generally at 10, is formed principally a sole assembly indicated generally at 12, and a shoe upper or upper assembly indicated generally at 14. The sole assembly 12 includes an outer sole 16 of a wear-resistant material such as rubber or similar plastic material and has a non-slip bottom surface with a tread or crepe pattern. An insole or inner sole 18 is bonded to the upper surface 16A of the outer sole 16 by a thin layer of adhesive 20 and such construction follows that of the patents identified above. The insole 18 is of generally the same thickness over the full extent of the insole. The outer sole 16 is somewhat wedge shaped, tapering from a thickened portion near the heel H of the shoe in the direction of the toe T. The sole assembly 12 is symmetrical relative to a vertical plane passing through the longitudinal axis of the shoe 10.

The upper 14 is secured to the upper surface 16A of the outer sole 16 by adhesive bonding in similar fashion to that of the shoes identified above. The upper is formed principally of an outer wall 24 of a substantially elastic, flexible material such as a NYLON® mesh and interior lining of a soft, conformable material such as plastic foam 26 laminated thereto, the lining 26 being bonded to the inner face of the outer wall 24.

The upper 14 extends along the heel H and sides S of the shoe and like the medical shoes of the patents identified above, has an open toe 31. A narrow trim strip 28 is secured as by sewing, with the stitches illustrated at 30, along the outer edges of the upper. Further, an arch-shaped trim strip 28' is sewn onto the sides S and heel H of the shoe upper extending from the upper surface 16A of the outer sole 16 from one side S of the shoe to the other. In a forward direction, the sides S of the upper 14 include integral flaps 34,. 36, the flaps as seen best in FIG. 5 being of a length such that flap 36 overlaps flap 34 to a small extent. The present invention advantageously employs a hook and loop type fastener system 37. The fastener system 37, FIG. 1, eliminates the need for straps and rings associated with U.S. Pat. Nos. 4,677,767 and 5,138,777. The hook and loop type fastener system 37 is formed by a pair of diagonal strips of fabric as at 38 fixed to outer surface 24 of the shoe upper and has appropriately, loops facing outwardly from the outer surface 24 thereof. The strips 38 extend upwardly from the upper surface 16A of the outer sole 16 on flap 34, to the edge of the flap 34 bearing the trim strip 30. The strips 38 are spaced from each other and extend diagonally, parallel to each other. Applied to the bottom surface of flap 36 is a generally half-moon strip 40 of an opposite type hook like VELCRO®material, with the hooks thereof engaging the loops and securely fastened to the loops on the outer surface of companion VELCRO® material strips 38. The strips 38 and the half-moon strip 40 are secured by suitable adhesive respectively to the outer surface 24 of flap 34 and the inner surface of flap 40 adjacent trip strip 28 of flap 40. The fastener strip 40 is generally at right angle to the longitudinal axes of diagonal strips 38. The hook and loop type fastening strips are sold under the VELCRO® trademark, and these strips are similar to that material integrated to the straps in the post-operative shoes of the patents cited above.

The existence of buckles, rings and the like in the past have caused pressure sores of the dorsum of the foot, further, the doctor treating the patient or nurses or other aides, or the patient himself, may readily disengage one flap from the other to facilitate putting on and taking off of the medical shoe.

By eliminating the need for exterior straps and buckles or rings, there is significant reduction in the incidence of pressure sores on the dorsum of the foot while providing a complete cover for the dorsal (top) aspect of the foot F.

A further important aspect of the invention lies in the incorporation of metatarsal shank 22 formed of a high density, low flexibility elastomer material of a length sufficient to fully support the metatarsal-phalange joints after trauma or surgery and to help reduce pressure to the plantar aspect of the foot F. Such metatarsal shank 22 may be molded integrally into the outer sole 16, with the metatarsal shank 22 in proximity to or flush with the upper surface 16A of the outer sole 16. Alternatively, the metatarsal shank 22 may be interposed between the soft insole 18 and the outer sole 16 with appropriate accommodation in tile thickness of the insole 18 to eliminate the presence of a hump due to the introduction of the metatarsal shank 22. The metatarsal shank 22 may have a planar configuration matching that of the outer sole 16 and may be of a width equal to the width of the outer sole 16 in the area of its location, or may be slightly narrower than the outer sole 16.

Figure 4:
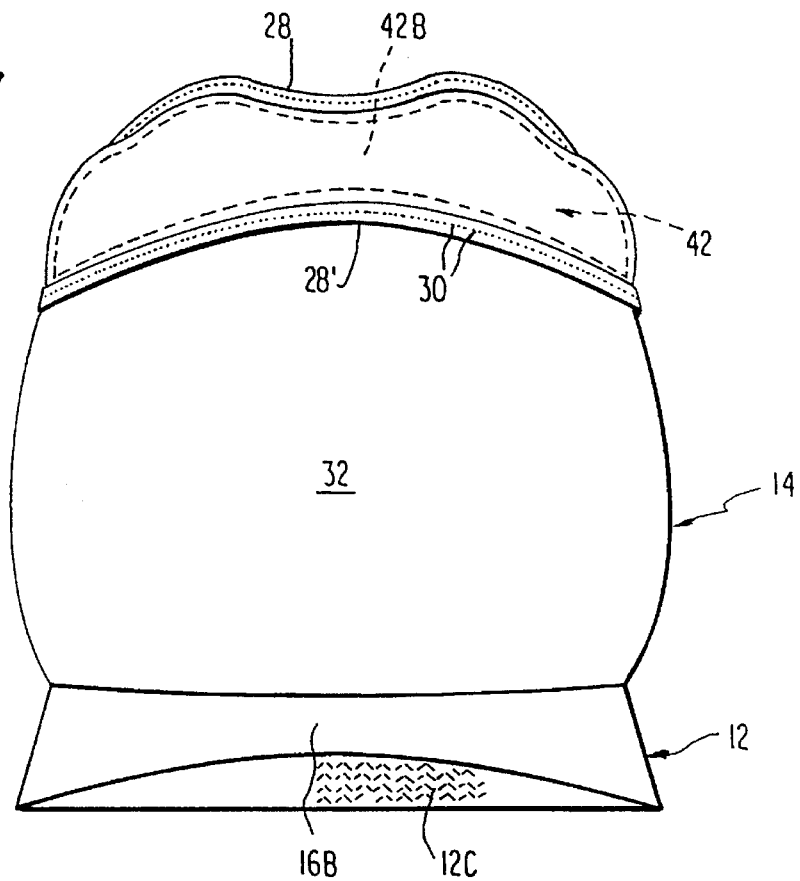
FIG. 4 is a rear view of the shoe of FIG. 1 showing the heel cup and heel collar.

A further important aspect of the present invention resides in the incorporation of a full-length heel collar indicated generally at 42, FIG. 1, in which only one-half of the heel collar is shown, the opposite being a mirror image thereof. The heel collar 42 is of arcuate form, extending the full vertical height of the upper 14 at the heel H, and following the curvature of the arcuate trim strip 28' about the periphery of the heel cup 32, with collar consisting of a pair of near vertical leg portions 42A, merging with an integral central portion 42B, which as seen in FIG. 4, creates a visible bulge within the shoe upper 14 above a generally rigid material heel cup 32. The heel collar 42 conforms to the concave area between the achilles tendon of the patient and the malleoli known as the Achilles Triangle. By constructing the heel collar of a relatively thick foam core member 48 covered with a breathable, non-irritating material 50 which contacts the skin of the patient and, due to the full-length arcuate structure 42, the heel collar acts to reduce any tendency for the heel to slip within the heel cup 32.

The heel collar 42, as designed, renders it virtually impossible for the patient to experience heel slippage during ambulation of the foot F. This problem has been evident in all heretofore known post-operational shoes due to the method of closure of the shoe, the lack of a toe box, the presence of bulky forefoot dressings, and the relative rigidity of the shoe. By fitting the full-length heel collar 42 in the position shown, due to its arch configuration, and by bonding it by means of adhesives, such as adhesive 20, over the contact surface of the heel collar 42 facing the soft lining 26 of the upper 14, the anti-heel slip feature is accomplished without adversely effecting the comfort of the patient while wearing the shoe 10. The inner soft foam body or core 48 is surrounded by the breathable, non-irritating material cover, and as illustrated at 50, FIG. 5, is broken away to show the thick foam body 48 internally of that cover and which in turn is directly bonded to the soft foam material 26, lining the open mesh outer wall 24 of shoe upper 14.

Figure 5:
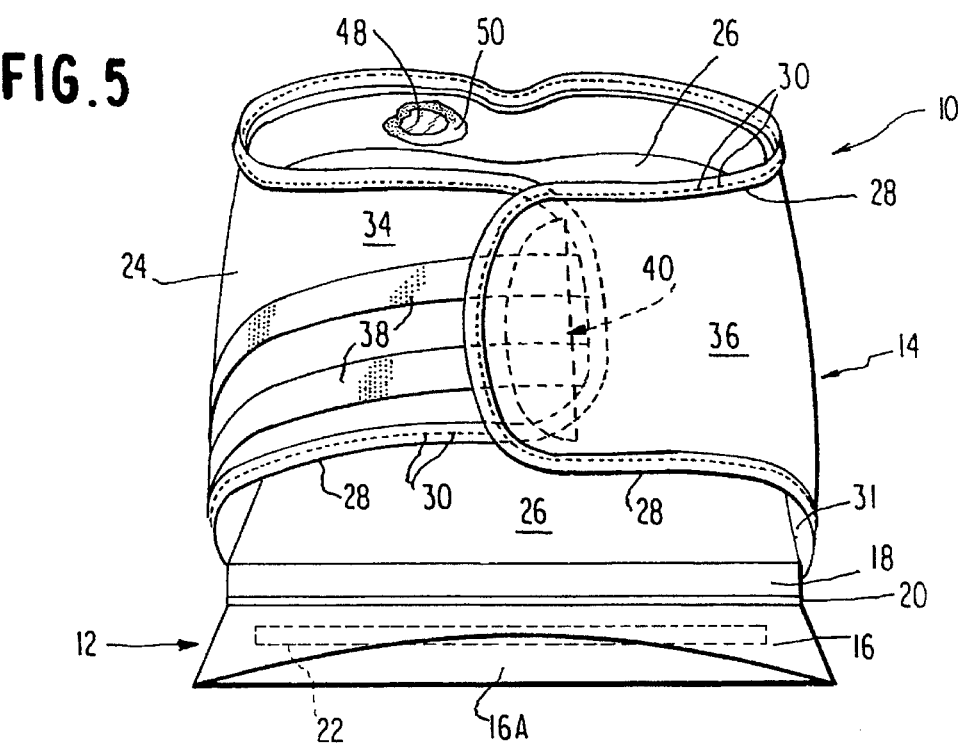
FIG. 5 is a from view of the shoe of FIG. 1 showing the fold-over flaps and rounded sole.

The front edge of the sole assembly 12, FIG. 5, is flat and vertical, as at 18A for the insole 18, and 16A for the outer sole 16 bonded thereto. The rear 18B of the insole 18 lies internal of the heel cup 32 as does the major extent of the insole 18 except for that at 18A, exposed by the open toe opening 31. The rear 16B of the outer sole 16 is also flat and extends horizontally from one side edge of the outer sole 16 to the other.

The bottom surface of the sole assembly 12, defined by the outer sole 16, is formed of three sections: a first, front section 12A over a length D1, which is curved upwardly and forwardly; an intermediate section 12B which is flat and of a length D2; and a curved rear section 12C of length D3, which extends rearwardly and upwardly with a greater curvature than that of section 12A. The curved rear section 12C extends over a distance D3, which is essentially the same distance as D1 for the front curved portion 12A. The sections 12A and 12C are of about the same length and both of those are approximately one-half the length of the flat intermediate section 12B.

It may be appreciated that the outer sole 16 is constructed with a rounded heel and toe allowing the patient to roll gently into and out of the gate cycle, further reducing stress to the heel or forefoot. The outer sole 16 is of single, injected-molded elastomer with an aggressive tread design to provide better traction, and has embedded therein, the metatarsal shank 22.

As it may be appreciated from the above description, the medical shoe 10 of this invention effectively supports a post-operative, traumatized, diabetic or sensitive foot F and being formed of a sole assembly which includes a shock-absorbing resilient outer sole having bonded thereto an insole of shock-absorbing foam that contours to and supports the sole of the foot F. The outer sole has its flexibility regulated by the preferably encapsulated metatarsal shank to limit the amount of flexibility under the metatarsal phalangeal joint. Further, the outer sole is of a special rocker design which allows the patient or wearer to roll through the gate cycle without placing undue pressure on the heel and forefoot. The upper is formed of an outer wall of breathable nylon mesh material lined with a soft conforming foam plastic material, preferably reinforced at the heel by a heel cup insert that provides lateral stability and is lined at the top and downwardly via an arch structure constituting a full-length heel collar that conforms to the Achilles Triangle, thereby providing padding to the achilles tendon and under the malleoli, rendering it virtually impossible for the heel of the foot to slip out of the shoe tendering ambulation.

The shoe of this invention is further characterized by the forward portion of the upper, which utilizes two flaps that extend upwardly on respective opposite sides of the front of the foot and fasten onto each other by means of a hook and loop type fastener system sold under the registered trademark VELCRO®, eliminating the need for exterior straps and buckles which in the past have caused pressure sores on the dorsum of the foot while providing a complete cover for the dorsal (top) aspect of the foot F.

It will be understood that, while a preferred embodiment of the invention has been shown and described, changes and additions may be made therein and thereto without departing from the spirit of the invention. Reference should accordingly be had to the appendant claims in determining the true scope of the invention.

What is claimed is:

1. In a surgical shoe adapted for use on a post-operative foot comprising:

a sole assembly including an outer sole having a greater thickness in a heel region and tapering in a direction towards a toe region, said outer sole having a degree of flexibility similar to that of a conventional running shoe sole assembly;

an inner sole conforming generally to the plantar aspect of the foot; and an upper assembly secured to the sole assembly and adapted to surround the heel, sides and dorsal portions of the foot, having an open toe region, and having a forward portion of said upper assembly divided into left and right flaps adapted to cover the dorsal region of the foot;

the improvement comprising a low flexibility elastomer metatarsal shank between the inner and outer sole, underlying the metatarsal-phalange joints of the foot and being of a length sufficient to support the metatarsal-phalange joints and to help reduce pressure to the plantar aspect of the foot, and wherein said metatarsal shank is of a width generally on the order of the width of said outer sole and being of an elastomer having greater rigidity than that of the outer sole, thereby limiting the flexibility of the outer sole under the metatarsal-phalange joint, the outer sole having a bottom surface consisting of a flat intermediate section, a front, forwardly and upwardly curved section, and a rear upwardly and rearwardly curved section, allowing a wearer of the shoe to roll through the gait cycle without placing undue pressure on the heel and forefoot, and wherein the length of the intermediate section is approximately twice that of either the front section or the rear section, and the front and rear sections are of approximately the same length, and said medical shoe further comprises a heel cup of relatively rigid material within the upper assembly, being of generally arcuate form and extending upwardly from the upper surface of the outer sole to provide lateral stability to the upper assembly and being lined at the top of the upper, across the heel cup of the shoe and downwardly with an arched full length heel collar terminating in laterally opposite leg portions integral with a central portion extending across the heel cup, and wherein said heel collar comprises a relatively thick foam core member conforming to the achilles triangle of the user's foot and reducing any tendency of the heel of the foot to slip within the heel cup, thereby rendering it virtually impossible for the user to experience heel slippage during ambulation of the foot.

2. The medical shoe as claimed in claim 1, wherein said relatively thick foam core member is covered with a breathable, non-irritating sheet material on the surface of the core member facing the skin of the user to further minimize the tendency for the heel to slip within the heel cup during ambulation.

* * * * *